(12) United States Patent
Schmitt et al.

(10) Patent No.: US 7,281,439 B2
(45) Date of Patent: Oct. 16, 2007

(54) VOLATILE ORGANIC COMPOUND MONITORING

(75) Inventors: Clifford T. Schmitt, Fall City, WA (US); Richard W. McManus, Issaquah, WA (US); Peter D. Jewett, Fall City, WA (US); J. Riley Conkin, Bellevue, WA (US)

(73) Assignee: HVOC, L.L.C., Issaquah, WA (US)

( * ) Notice: Subject to any disclaimer, the term of this patent is extended or adjusted under 35 U.S.C. 154(b) by 146 days.

(21) Appl. No.: 10/800,458

(22) Filed: Mar. 15, 2004

(65) Prior Publication Data

US 2004/0177672 A1 Sep. 16, 2004

Related U.S. Application Data

(60) Provisional application No. 60/454,922, filed on Mar. 13, 2003.

(51) Int. Cl.
*G01N 1/00* (2006.01)
*G01N 33/18* (2006.01)

(52) U.S. Cl. .......................................... 73/863; 73/19.1

(58) Field of Classification Search ................. 73/19.1, 73/31.7, 864.73, 864.72, 864.34, 863
See application file for complete search history.

(56) References Cited

U.S. PATENT DOCUMENTS 4,452,091 A * 6/1984 Richers ................... 73/864.52
4,807,707 A * 2/1989 Handley et al. ............... 175/20
5,150,622 A * 9/1992 Vollweiler ............... 73/864.74
5,587,538 A * 12/1996 Bratton ..................... 73/863.33
5,922,950 A * 7/1999 Pemberton et al. ....... 73/152.28
6,000,481 A * 12/1999 Heller et al. ................... 175/20
6,230,820 B1 * 5/2001 Cordry .......................... 175/20
6,289,714 B1 * 9/2001 Tartre ...................... 73/864.74
6,405,135 B1 * 6/2002 Adriany et al. ................. 702/5
6,666,068 B2 * 12/2003 Boyd et al. ................. 73/31.07
2001/0035057 A1 * 11/2001 Jackson et al. ........... 73/863.83

\* cited by examiner

*Primary Examiner*—Hezron Williams
*Assistant Examiner*—John Fitzgerald
(74) *Attorney, Agent, or Firm*—Black Lowe & Graham PLLC (57) ABSTRACT

A system, method and apparatus for monitoring the subsurface at facilities for the presence of volatile organic compounds (VOCs). A surface penetration is made in a facility surface providing access to the subsurface soil beneath the facility. A soil probe is placed in communication with the soil beneath the facility surface and used to withdraw samples of soil gas from the pore space within the soil. The soil probe includes a monitoring port configured to seal the surface penetration and minimize the movement of undesirable materials between the facility and the subsurface via the monitoring port. The soil probe has an end filter in communication with the subsurface under the facility. The monitoring port is coupled to a sampling pump used to withdraw the soil gas sample. Soil gas samples are periodically obtained and analyzed for the presence of VOCs.

4 Claims, 10 Drawing Sheets

VOLATILE ORGANIC COMPOUND MONITORING

PRIORITY CLAIM

This application claims priority from U.S. Provisional Application Serial No. 60/454,922, filed Mar. 13, 2003, which is hereby incorporated by reference.

FIELD OF THE INVENTION

This invention relates generally to environmental pollution monitoring and, more specifically, to a system, method and apparatus for monitoring subsurface levels of volatile organic compounds (VOCs).

BACKGROUND OF THE INVENTION

Numerous commercial and industrial businesses use VOCs in day-to-day operations. Many of these VOCs are dangerous to human health and the environment if released to soil and groundwater. For example, the dry cleaner industry has historically used a variety of solvents in the cleaning process, including volatile organic solvents such as kerosene, Stoddard solvent, gasoline, propylene glycol ethers and carbon tetrachloride. More recently, the majority of dry cleaner operations use tetrachloroethene or perchloroethene (PCE) as a cleaning solvent. This VOC is a known cancer-causing agent in animals and may cause cancer in humans. Almost 95% of dry cleaner facilities use PCE in their cleaning processes.

When released and allowed to seep into the ground even small quantities of PCE can contaminate large quantities of soil and groundwater at levels dangerous to human health and the environment. Government prescribed cleanup levels for PCE are as low as 0.05 milligrams per kilogram in soil and 5 micrograms per liter in groundwater. A release of one gallon of PCE can contaminate 100 million gallons of groundwater to twice the prescribed cleanup level, and result in cleanup liability of hundreds of thousands and potentially millions of dollars.

Given the liabilities associated with contamination cleanup, the insurance industry has been reticent to insure real estate against environmental risks where dry cleaner operations are ongoing or have previously occupied space on the property. Property owners are unable to sell properties or can only sell at reduced prices because of the risk associated with owning properties previously occupied by dry cleaner operations. Other businesses that use, store or treat or recycle VOCs, such as metal plating and fabrication plants, are affected similarly.

Currently there is no practical system or method to periodically monitor, in an efficient and cost effective manner, the subsurface at business facilities where VOCs are used. Typically, subsurface investigations occur only when an audit, insurance review or property sale takes place, or when a large release is documented. These investigations generally involve installing soil borings and groundwater monitoring wells to determine if a release has affected the soil and/or groundwater. By the time an investigation is performed the damage is done and the problem could have been spread by groundwater flow to contaminate millions of gallons of groundwater and migrated beyond property boundaries. In addition, subsurface investigations involving soil borings and monitoring wells are expensive, with costs ranging to hundreds of thousands of dollars. Environmental professionals are required to design these investigations, manage boring and well installation, interpret data, and report results.

Thus, there is a need for an inexpensive system, method and apparatus to monitor facilities where VOCs are used to determine if a release has occurred. The monitoring will determine if problems already exist or will catch future releases in a timely manner to facilitate mitigation before the cost of cleanup escalates.

SUMMARY OF THE INVENTION

This invention is directed to a system, method and apparatus for periodically monitoring the subsurface at facilities where VOCs are used, stored and treated/recycled for releases of VOCs to the environment. This invention will enable business owners and property owners who lease space to business owners to protect their investment by monitoring the business operations. This invention will also provide insurers a means of assessing if a property has been affected by a release and monitoring insured properties to identify if a release has occurred such that the impacts can be mitigated before the contamination spreads and dramatically increases the costs associated with cleanup.

This invention involves the installation of one or more VOC monitoring systems at business operations where VOCs are used. A soil probe (or other VOC gas or vapor monitoring device) is placed so as to be in communication with the soil beneath the surface at a facility and used to withdraw samples of gas or vapor from the pore space within the soil. As used herein, the term soil gas and soil vapor are used interchangeably. Samples of the soil gas are analyzed for the presence of VOCs. VOCs released in the soil evaporate and diffuse within the pore space in the soil matrix. Samples of the gas removed from soil in the area of a VOC release will contain detectible concentrations of the VOC. Under facilities where no releases have occurred in close proximity to the soil probe, concentrations of the VOC should not be present in the soil gas. Where a release has occurred and migrated to soil in proximity to the soil probe, evidence of this release will be found present in the soil gas.

Implementing a protocol of periodic soil gas sampling at the facility is a cost-effective way to document whether ongoing operations have introduced VOCs into the soil matrix and groundwater, if present. Property owners and insurers benefit by knowing that year-to-year no releases to the subsurface have occurred. Property buyers benefit by knowing that the property is not being negatively impacted by ongoing operations. Business owners and insurers benefit by knowing that ongoing operations are not causing impacts to the property that would incur expensive liabilities.

BRIEF DESCRIPTION OF THE DRAWINGS

The preferred and alternative embodiments of the present invention are described in detail below with reference to the following drawings.

DESCRIPTION OF THE PRESENT INVENTION

Figure 1:
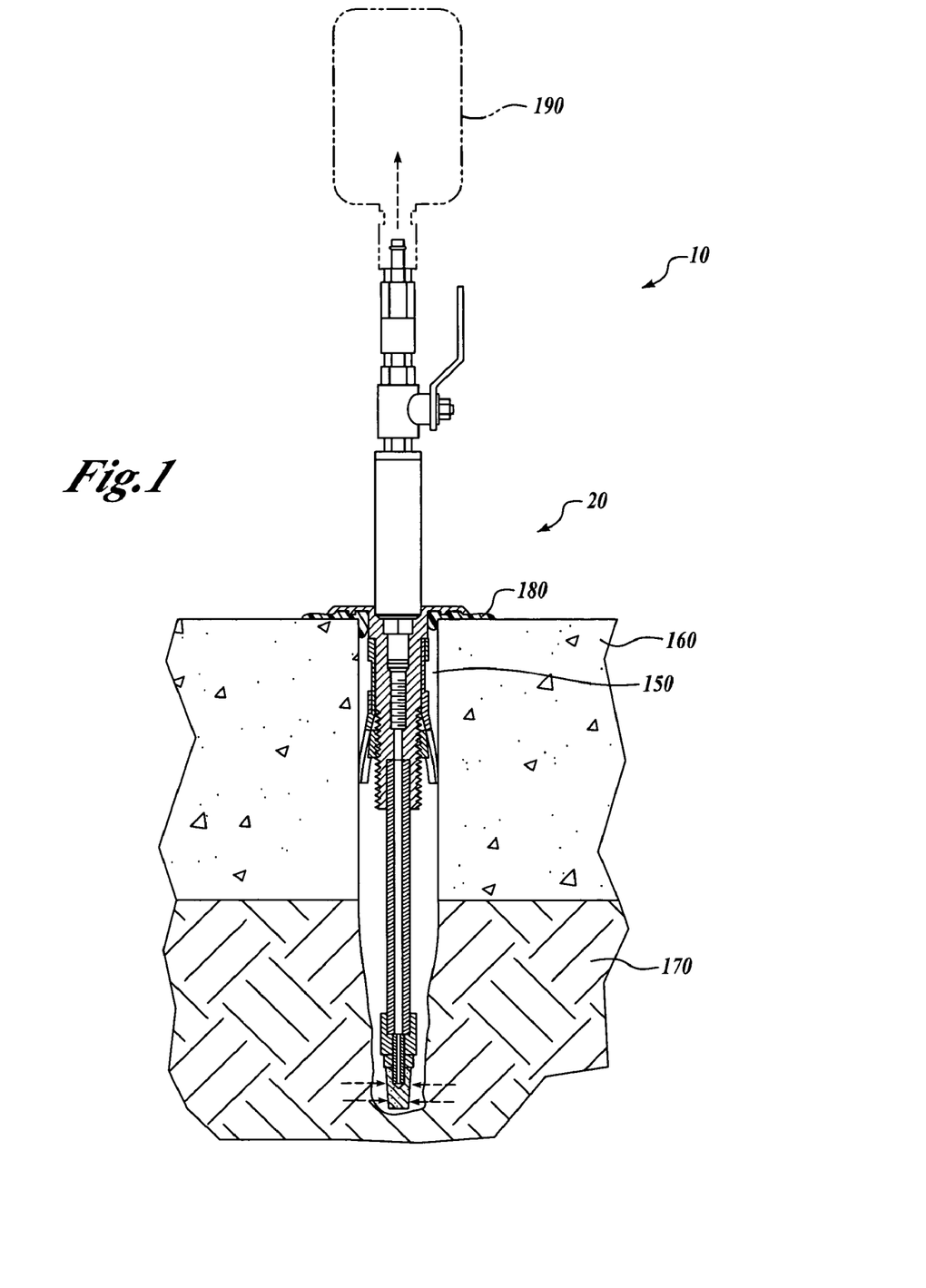
FIG. 1 is an illustration of the preferred embodiment of the system of the present invention.

The present invention is directed to a system, method and apparatus for monitoring subsurface levels of chemicals of concern or, in the preferred context of the present invention, volatile organic compounds (VOCs). With reference to FIG. 1, the preferred system 10 includes a soil probe 20 (or other VOC gas or vapor monitoring device) that is inserted through a surface penetration 150 in a facility surface 160, such as an interior building floor slab or an exterior facility surface such as parking lot, a sidewalk or concrete slab, to create access to the soil beneath the facility surface, referred to as the facility subsurface 170. Possible VOCs at the facility are prevented from seeping into the facility subsurface 170 through the surface penetration 150 by the installed soil probe 20 fixed in place, preferably by use of a VOC resistant epoxy sealant 180 or similar chemically resistant sealant between the soil probe and the facility surface.

Figure 2:
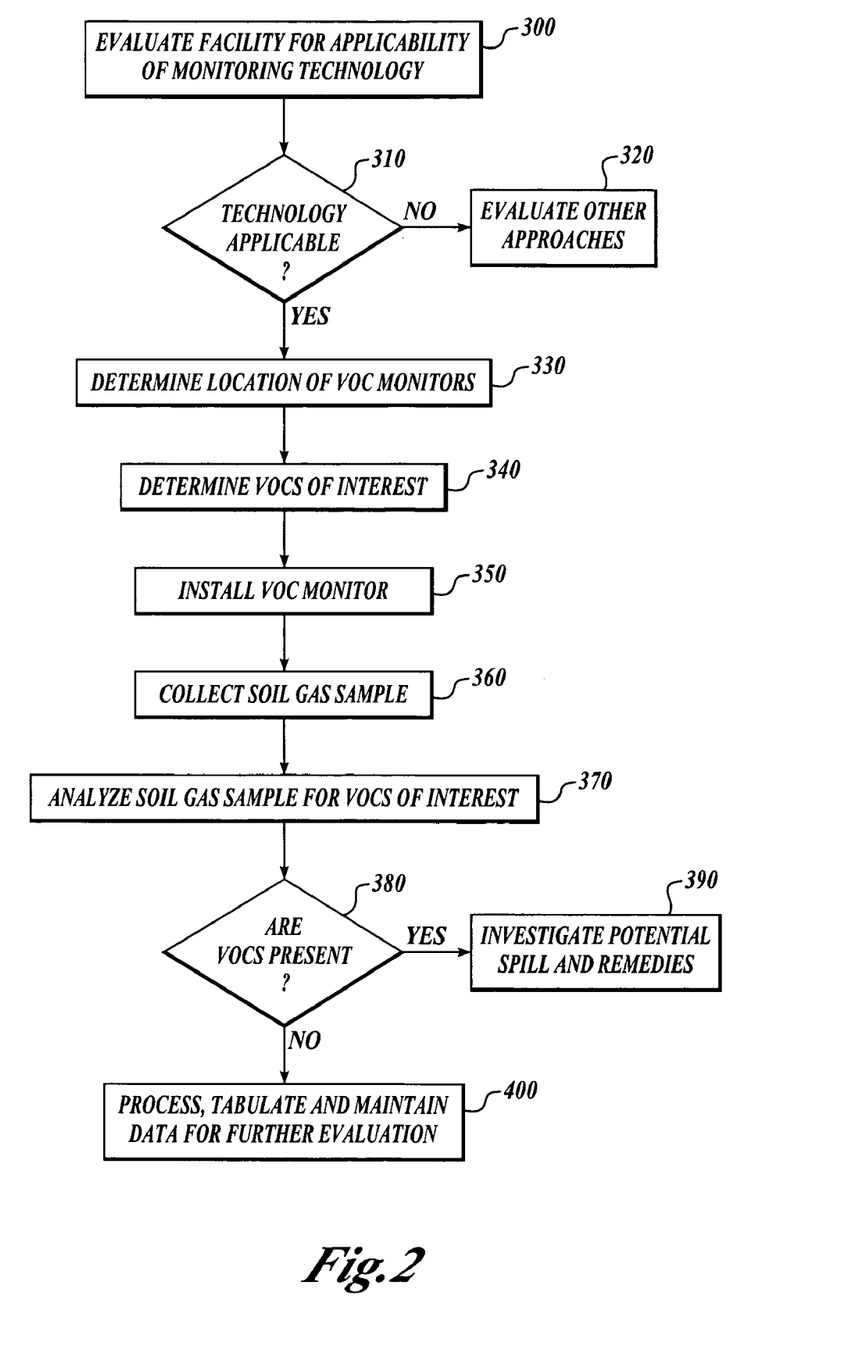
FIG. 2 is a flowchart showing the preferred VOC monitoring methodology of the present invention.

The methodology of the preferred embodiment for a monitoring system is described with reference to FIG. 2. At block 300, the facility is evaluated to determine the applicability of the VOC monitoring technology of the present invention. This step preferably involves an evaluation of the historical uses of the location, the chemical composition of VOCs that potentially may be released and the physical construction of the facility. At decision block 310, if the technology is determined not to be applicable, the logic proceeds to block 320, where other VOC monitoring technologies may be considered. If at decision block 310 the technology is determine to be applicable, the logic proceeds to block 330.

Figure 8:
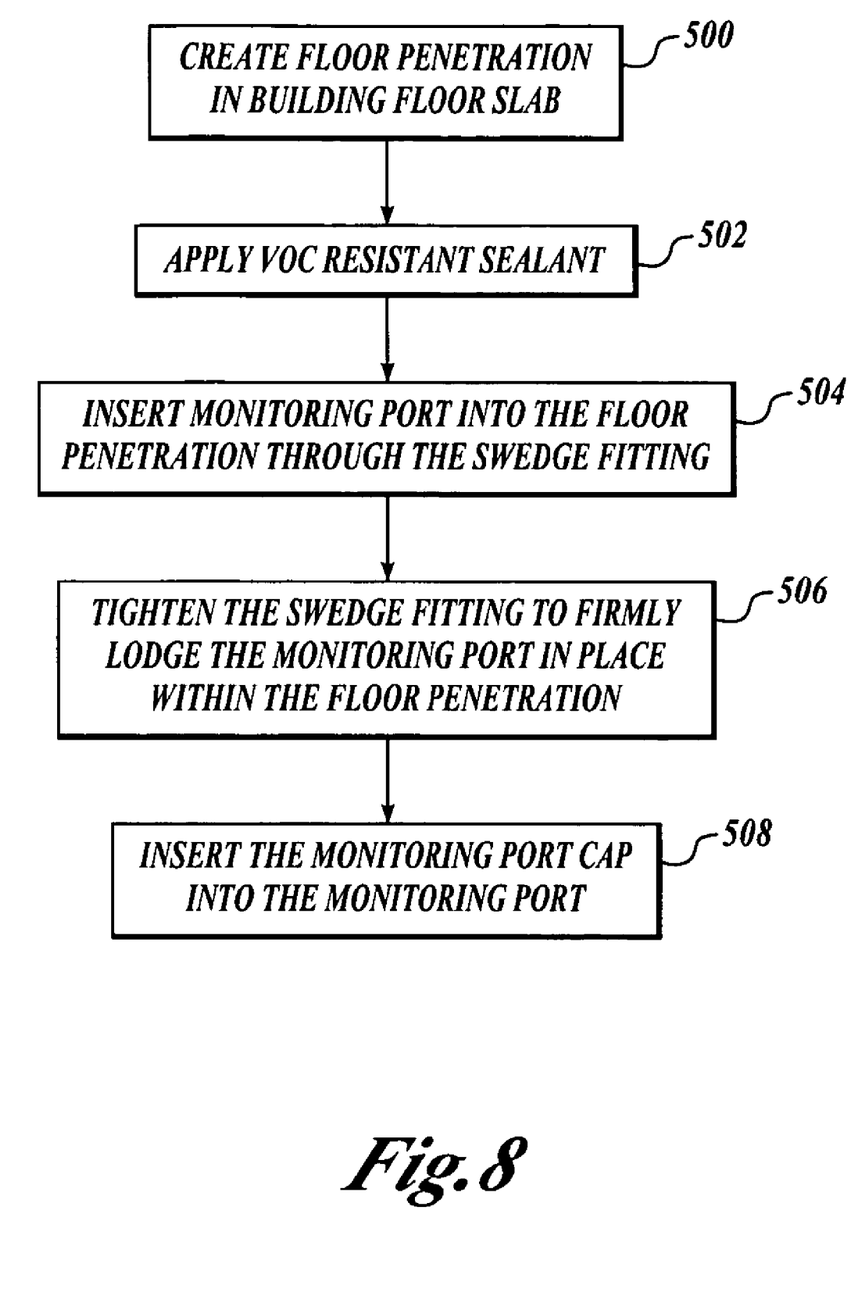
FIG. 8 is a flow chart showing the preferred VOC installation methodology of the present invention.

At block 330, the preferred location for the VOC monitor is selected. The present invention is preferably used at facility locations where VOCs are used, stored, or treated/recycled in commercial and industrial processes. This is preferably based on factors such as (1) the proximity to where VOCs are stored, used, treated, recycled, or disposed and releases are possible, and (2) the location where VOC release to the subsurface is made possible by facility structures, such as near construction joints, piping and storage containers. At block 340, the VOCs of interest are selected to facilitate proper sampling and testing. This step preferably involves determining what chemicals have been used at the facility and may have been released into the subsurface. The order of blocks 330 and 340 may be altered, or the steps performed simultaneously. At block 350, one or more VOC monitoring ports of the present invention are installed according the procedure described below with reference to FIG. 8.

At block 360, a soil gas sample is collected for analysis. This is preferably accomplished according to the procedure described below with reference to FIG. 9, and may be the initial assessment or part of an ongoing periodic or incidental monitoring program. At block 370, the soil gas sample is analyzed for selected VOCs of interest, either using field or laboratory methods. At decision block 380, a determination is made whether significant concentrations of VOCs are present. If significant concentrations of VOCs are present, the logic proceeds to block 390, where an investigation is commenced to determine whether a release of VOCs occurred and, if so, the nature of the release and preferred remedy. If no significant concentrations of VOCs are present, the logic proceeds to block 400, where data obtained during monitoring is processed, tabulated and maintained for future reference and continued evaluation. The definition of "significant concentrations" may be predetermined or determined during analysis, and may be based on a variety of factors, but preferably is characterized in part depending on the particular history of the property being evaluated and subsurface conditions such as soil type and presence of groundwater. For example, significant concentrations could include any concentration of VOCs in cases where previous monitoring found no concentrations to exist. Alternatively, significant concentrations could include only increases in concentrations of VOCs in cases where previous monitoring found low background levels to exist.

The preferred embodiment of the soil probe 20 is better understood with reference to FIGS. 1, 3 and 3A-3D. The preferred soil probe 20 consists of a monitoring port 30, a swedge fitting 60, an installation tool 70, a monitoring port cap 80, a cap tool 90 and a sampling adaptor 100, described in greater detail below.

Figures 3, 3A:
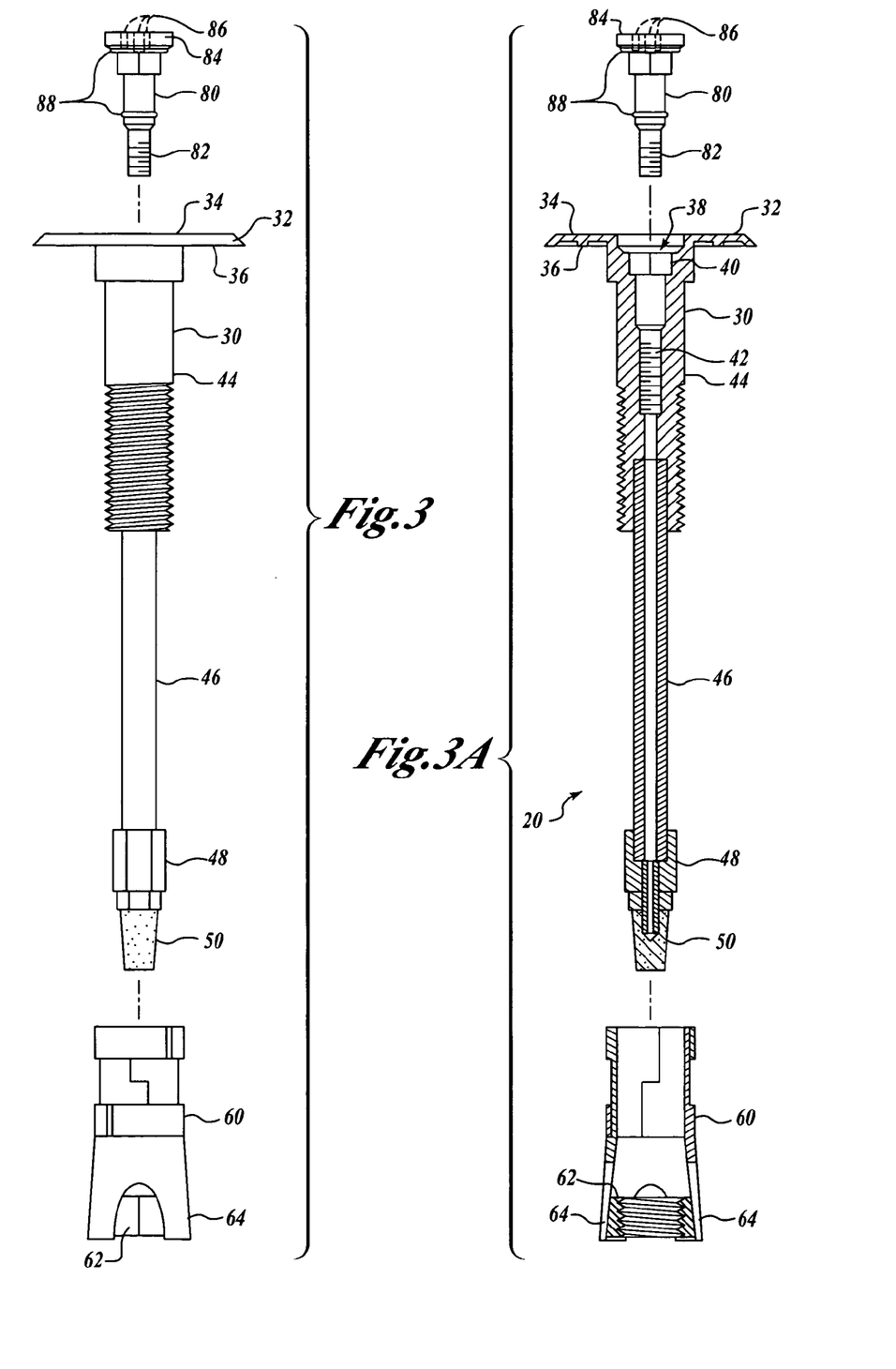
FIGS. 3, 3B, 3C and 3D are component views of the preferred embodiment of the soil probe of the present invention.
FIG. 3A is a partially exploded view of a monitoring port cap, monitoring port and swedge fitting of the preferred embodiment of the soil probe of the present invention.
Figure 3B:
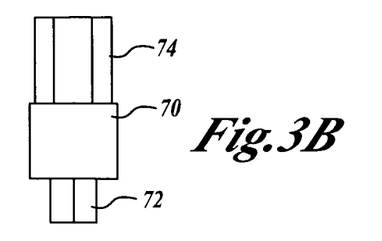
Figure 3C:
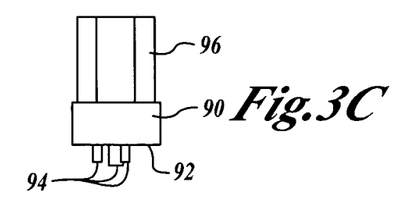
Figure 3D:
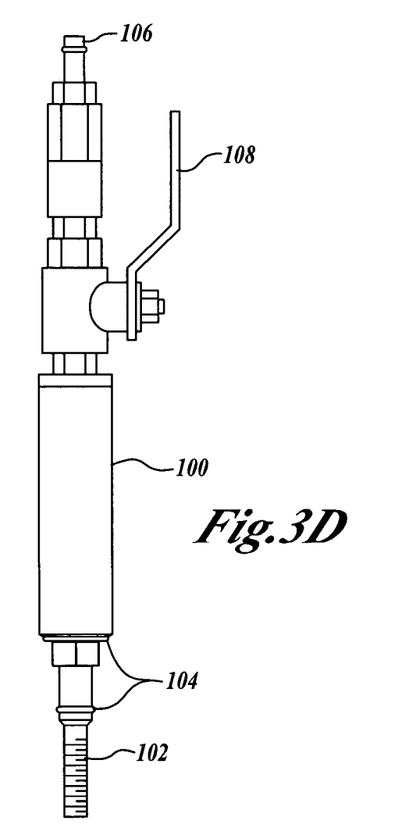
Figures 4, 4A:
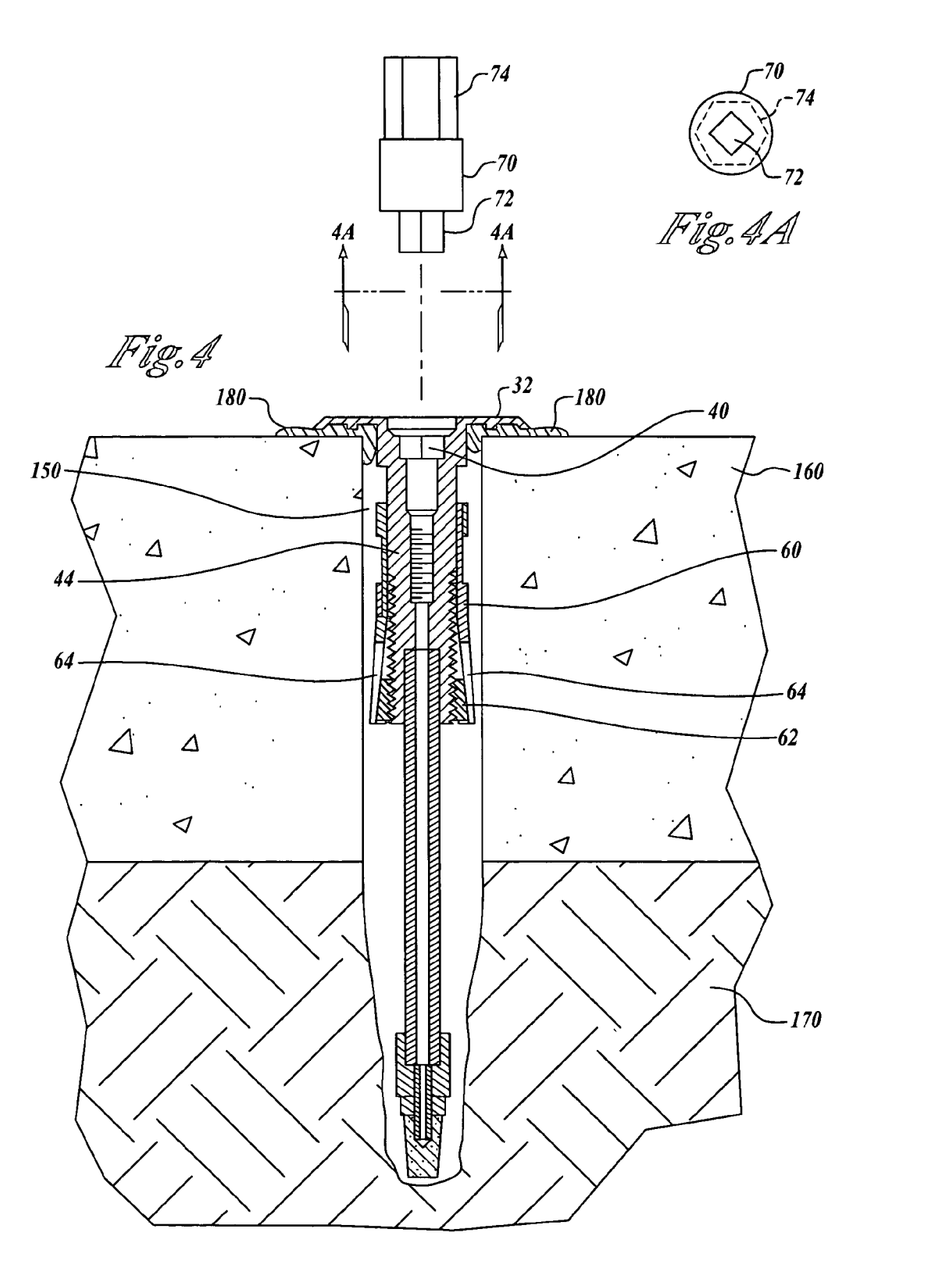
FIG. 4 is an illustration of an aspect of the installation of the preferred soil probe of the present invention utilizing an install tool.
FIG. 4A is an illustration of the bottom configuration of the install tool shown in FIG. 4.
Figure 5:
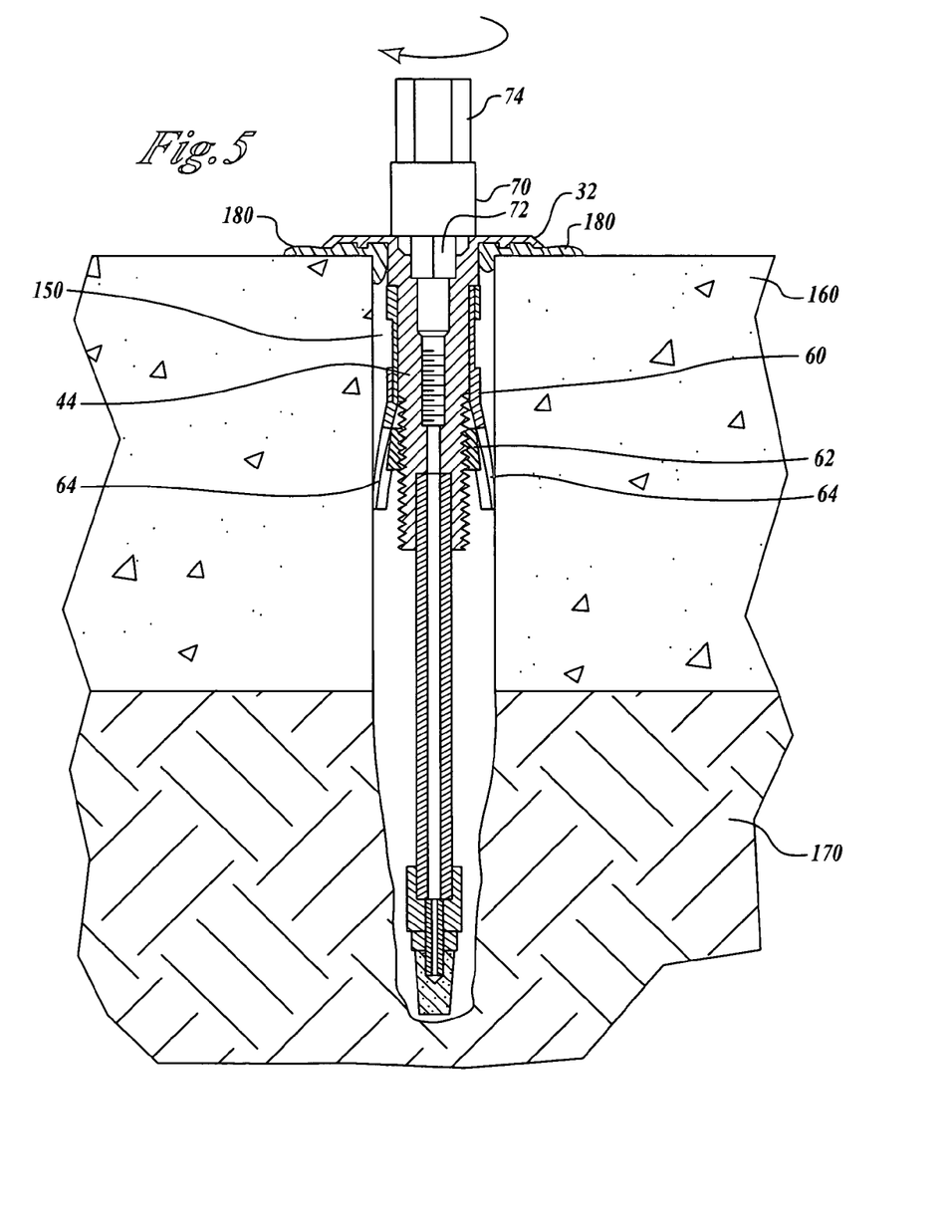
FIG. 5 is a further illustration of an aspect of the installation of the preferred soil probe of the present invention utilizing an install tool.
Figures 6, 6A, 6B:
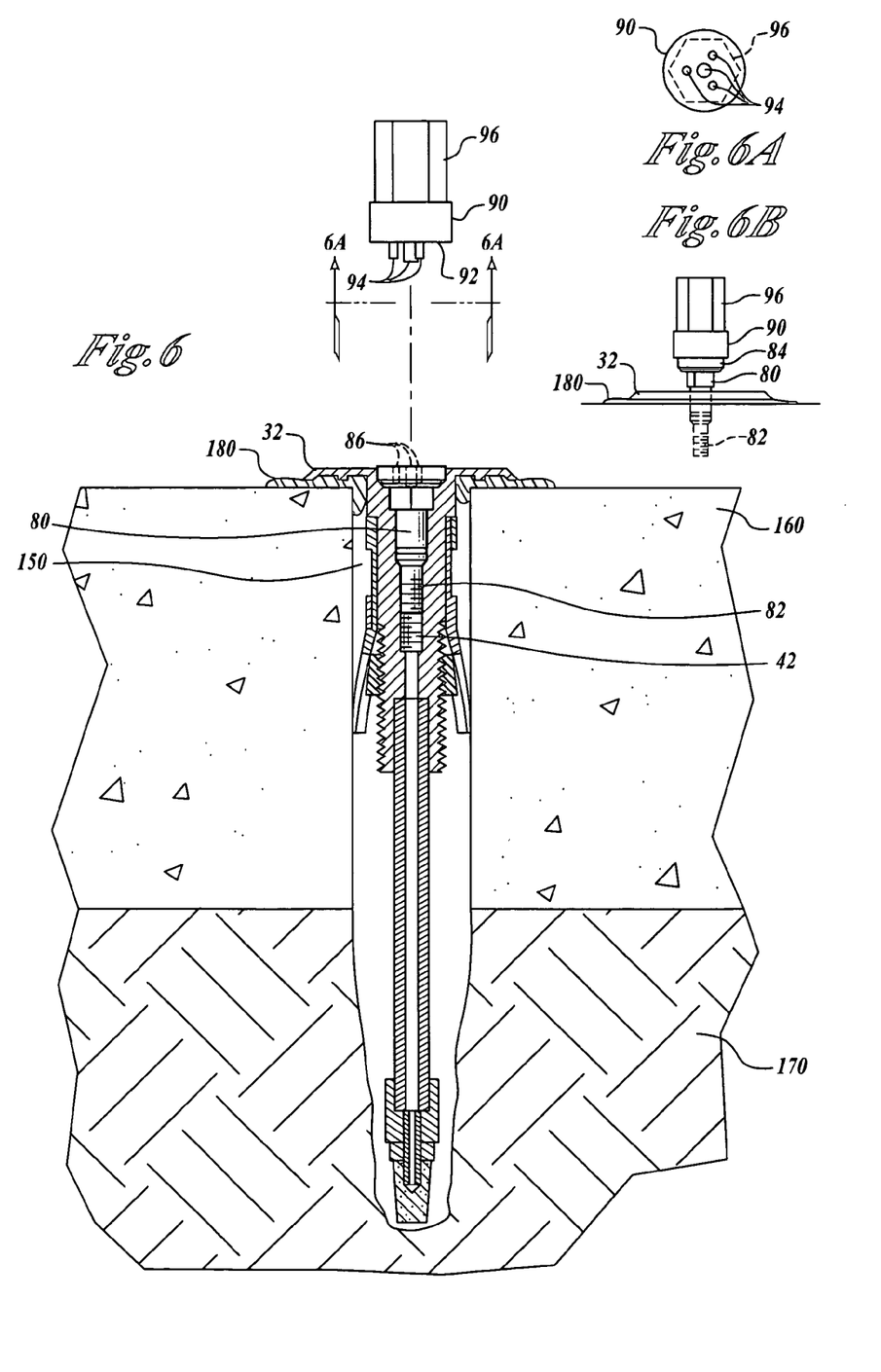
FIG. 6 is an illustration of an aspect of the installation of the preferred soil probe of the present invention utilizing a cap tool.
FIG. 6A is an illustration of the bottom configuration of the cap tool shown in FIG. 6.
FIG. 6B is an illustration of an aspect of the installation of the preferred soil probe of the present invention wherein the cap tool is used to install a monitoring port cap.

The monitoring port 30 is a substantially hollow, generally tubular-shaped member comprised of a head or mounting plate 32, a threaded neck 44, an extension tube 46, a thread adaptor 48 and an end filter 50. The mounting plate 32 is preferably larger in diameter than the tubular body of the probe in order to cover the surface opening of the surface penetration 150. The mounting plate 32 has a top side 34 and bottom side 36. As described with reference to FIG. 3A, the mounting plate 32 includes a threaded locking aperture 38 used to receive the installation tool 70, the monitoring port cap 80 or the sampling adaptor 100. The locking aperture 38 tapers from flush with the top 34 of the mounting plate to an interior locking groove 40 and then to a threaded interior 42. In an alternative embodiment, a one-way valve (not shown) may be installed in the interior of the threaded neck 44 to prevent VOCs or other contaminants from the facility atmosphere from passing through the monitoring port 30 into the subsurface 170 during operation of the system of the present invention.

The threaded neck 44 extends away from the bottom 36 of the mounting plate 32. The extension tube 46 extends from the end of the threaded neck 44 remote from the mounting plate 32. The extension tube may be of varying length depending on the penetration depth required for the probe, which in turn varies depending on the type of soil beneath the facility, the proximity to potential leaks or spills and the surface construction details. In an alternative embodiment, the length of the probe may be such that it does not extend beneath the bottom of the facility surface 160, for example, the bottom of a building floor slab. In this embodiment, the sample of soil gas is drawn from the pocket created between the facility surface 160 and the subsurface 170 by the surface penetration 150.

The thread adaptor 48 transitions between the end of the extension tube 46 remote from the threaded neck 44 and the end filter 50. The end filter 50 may be a screen, other porous material filter or simply holes in the soil probe designed to allow the passage of soil gas while restricting the passage of soil particles into the soil probe. The diameter of the probe is preferably less than one inch (2.45 cm), but may be larger in certain applications where a larger probe is desirable for engineering reasons.

The swedge fitting 60 has an interior nut 62 with threads corresponding to the threaded neck 44 of the monitoring port 30. As the threaded neck 44 is threaded through the swedge fitting, the sides 64 of the swedge fitting are forced outward to engage material adjacent the swedge fitting, thereby securing the swedge fitting in place. The install tool 70 has a locking end 72 corresponding in size and shape to the locking aperture 40 of the mounting plate 32 and a tightening end 74 preferably of a standard socket size and shape. The unique correspondence between the interior locking groove 40 of the mounting plate 32 and the locking end 72 of the install tool 70 in the preferred embodiment discourages inadvertent or unauthorized removal of the monitoring port.

The preferred embodiment, the monitoring port cap 80 has a threaded first end 82 that corresponds to the threaded interior 42 of the locking aperture 38 of the mounting plate 32 and a cap head second end 84 that includes turning recesses 86 preferably formed therein. The monitoring port cap 80 preferably includes a plurality of o-rings 88 designed to created a substantially airtight seal between the monitoring port cap 80 and the interior of the locking aperture 38 of the monitoring port 30 when the monitoring port cap is interfaced within the monitoring port. In alternative embodiments, the monitoring port cap 80 may be attached to the monitoring port 30 by means other than corresponding threads, for example, snap or friction fit. In yet an alternative embodiment, the monitoring port cap may be unitary with the monitoring port, for example, as a retractable piece providing access to the monitoring port 30. The cap tool 90 has a connection end 92 having turning pins 94 corresponding in size and shape to the turning recesses 86 of the monitoring port cap 80 and a tightening end 96 preferably of a standard socket size and shape. The unique corresponding pin-recess configuration between the cap tool 90 and the monitoring port cap 80 in the preferred embodiment discourages inadvertent or unauthorized removal of the monitoring port cap.

The sampling adaptor 100 is a hollow, generally tubular-shaped member having a threaded first end 102 that corresponds to the threaded interior 42 of the locking aperture 38 of the mounting plate 32. The sampling adaptor 100 preferably includes a plurality of o-rings 104 designed to created a substantially liquid and airtight seal between the sampling adaptor 100 and the interior of the locking aperture 38 of the mounting plate 32 when the sampling adaptor 100 is interfaced within the monitoring port 30. The sampling adaptor 100 has a second end 106 designed to interface with a sampling pump (represented as 190 in FIG. 1) into which soil gas samples are withdrawn from the facility subsurface 170. The sampling adaptor includes a shutoff valve 108 that opens and closes the tubular interior path between the first end 102 and the second end 106.

Other VOC monitoring devices, for example, electronic detectors, could be used to perform the function of the soil probe 20. In addition, the soil probe may take various forms without departing from the scope of the present invention. For example, the soil probe may consist of a hollow tube with a closed end, manufactured with small diameter holes or slots along its length for the intake of gases from the subsurface 170. The holes can vary in size and spacing depending on the soil being penetrated for sampling and monitoring. This embodiment effectively merges the monitoring port 30 and sampling adaptor 100 components into a single, monolithic member or monitoring station. The resulting monitoring station would preferably have a first monitoring end through which soil gas samples could be drawn and a second sampling end adaptable to a sampling pump or other device designed to withdraw and capture a soil gas sample. Yet other embodiments, for example incorporating the use of one or more screens rather than holes or slots along a hollow tube, may also be used.

A preferred method for installing the preferred soil probe 20 of the present invention is described with reference to FIGS. 1, 3-6 and 8. With reference to the flow chart shown in FIG. 8, at block 500, a small diameter surface penetration 150 is made in the facility surface 160 to allow installation of the soil probe. This may be accomplished by drilling or other means. At block 502, a VOC resistant epoxy sealant 180 or similar chemically resistant sealant is placed around the surface penetration 150 on the facility surface 160.

At block 504, the monitoring port 30 is inserted through the surface penetration 150 so as to be in communication with the facility subsurface 170 beneath the facility surface 160. In the preferred embodiment, this is accomplished by threading the threaded neck 44 of the mounting plate 32 through the threads of the interior nut 62 of the swedge fitting 60. The mounting plate 32 is pressed securely via the VOC resistant epoxy sealant 180 to the facility surface 160 as it is threaded into the swedge fitting within the surface penetration. At block 506, the monitoring port 30 is tightened within the swedge fitting 60 to firmly lodge the monitoring port in place within the surface penetration 150. As better described with reference to FIGS. 4, 4A and 5, the locking end 72 of the install tool 70 is inserted into the locking aperture 40 of the mounting plate 32. Using a socket wrench or other tightening means, the tightening end 74 is twisted, thereby further threading the threaded neck 44 along the threads of the interior nut 62 of the swedge fitting 60. As the threaded neck 44 is threaded through the swedge fitting, the sides 64 of the swedge fitting are forced outward to engage material adjacent the swedge fitting, in this case the facility surface 160, for example, within the surface penetration of a building floor slab, thereby securing the swedge fitting and monitoring port in place within the surface penetration. Alternative fittings or other securing methods may be used to secure the monitoring port in place within the surface penetration. For example, locking clamps, tightening bolts or expanding fittings may be used instead of a swedge fitting. In addition, sealants, glues or filling material may be placed between the monitoring port and the facility surface to secure the monitoring port in place within the surface penetration.

As described above, the bottom side 36 of the mounting plate 32 is sealed to the facility surface 160 using the VOC resistant epoxy sealant 180 to preferably eliminate leakage of VOCs or other contaminants from the facility into the subsurface 170 beneath the facility surface 160 via the surface penetration 180 and to seal in soil gas that may contain VOCs or other contaminants. In addition, in facilities where VOCs are used, stored, treated/recycled there will be measurable concentrations of VOCs in the air. It is necessary to seal out these VOCs from being drawn into the soil beneath the slab during or between sampling events.

At block 508, the monitoring port cap 80 is inserted into the monitoring port 30. More specifically, the threaded first end 82 of the monitoring port cap 80 is threaded along the threaded interior 42 of the locking aperture 38 of the mounting plate 32. This is preferably accomplished using the cap tool 90. As shown with reference to FIGS. 6, 6A and 6B, the turning pins 94 of the cap tool 90 are aligned with and inserted into the corresponding turning recesses 86 of the monitoring port cap 80 and the cap tool (or other tightening means) is used to thread the threaded first end 82 of the monitoring port cap along the threaded interior 42 of the mounting plate 32. A substantially liquid or airtight seal is preferably created between the monitoring port cap 80 and the monitoring port 30 by virtue of the plurality of o-rings 88 (see FIGS. 3 and 3A).

Alternative embodiments of the soil probe 20 can be installed using any of a variety of methods, for example, through vibratory insertion or manual force in a retrofit application or forming the soil probe into the facility surface at the time of construction. The top of an alternative soil probe is terminated along the top of the facility surface at an access port, which is a port sealed in the surface penetration and designed to prevent any possible leakage of released VOCs or other contaminants. The access cover, door, hatch, or other means of opening the monitoring port is also sealed between uses to prevent any possible leakage through the monitoring port by use of o-rings, sealants or other means. As described above, in the preferred embodiment, the soil probe that penetrates the subsurface is installed with a manual valve or quick-connect self-sealing valve to prevent possible chemical leakage through the sampling port as well as to seal in soil gas that may contain VOCs or other contaminants.

Figure 7:
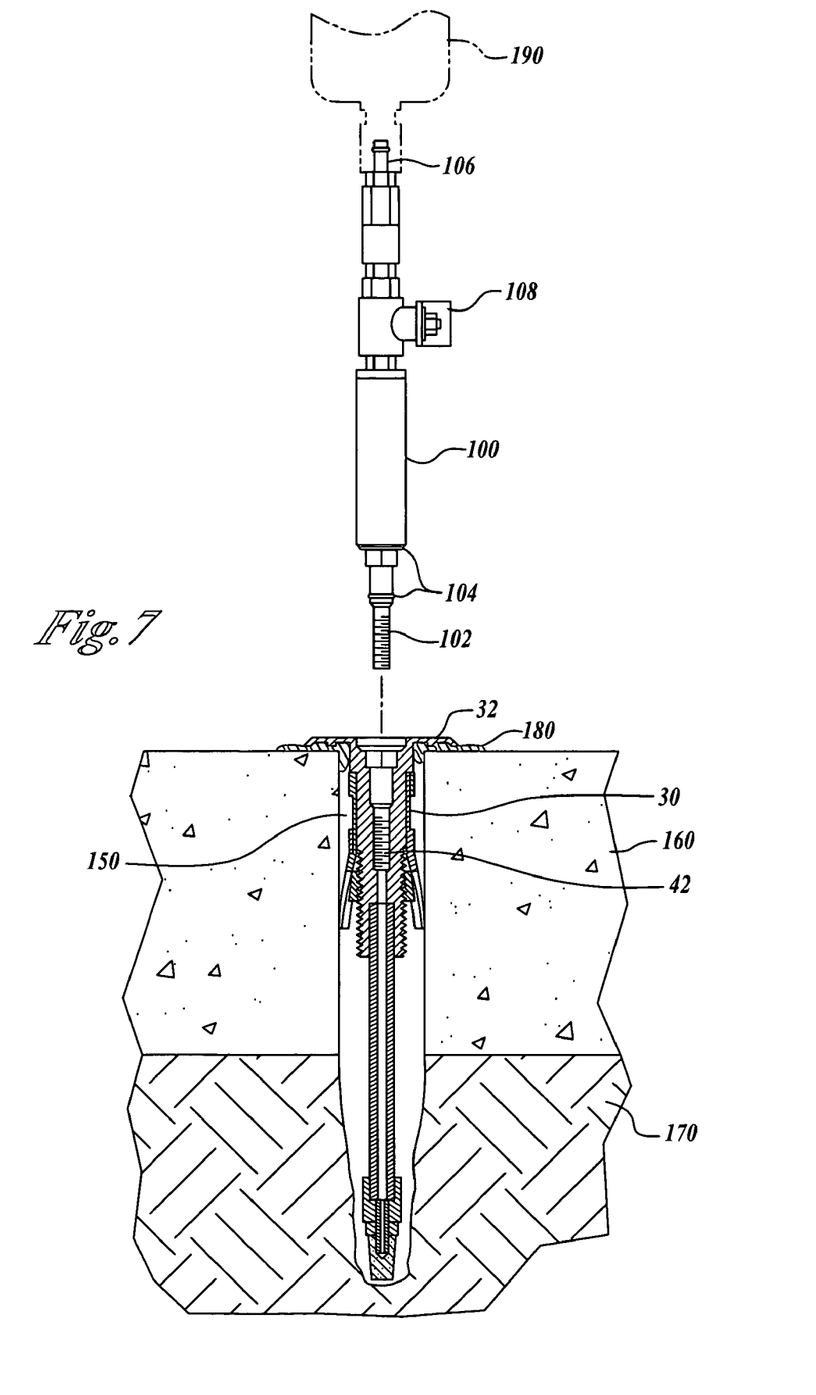
FIG. 7 is an illustration of an aspect of the VOC monitoring process utilizing a preferred sampling adaptor.
Figure 9:
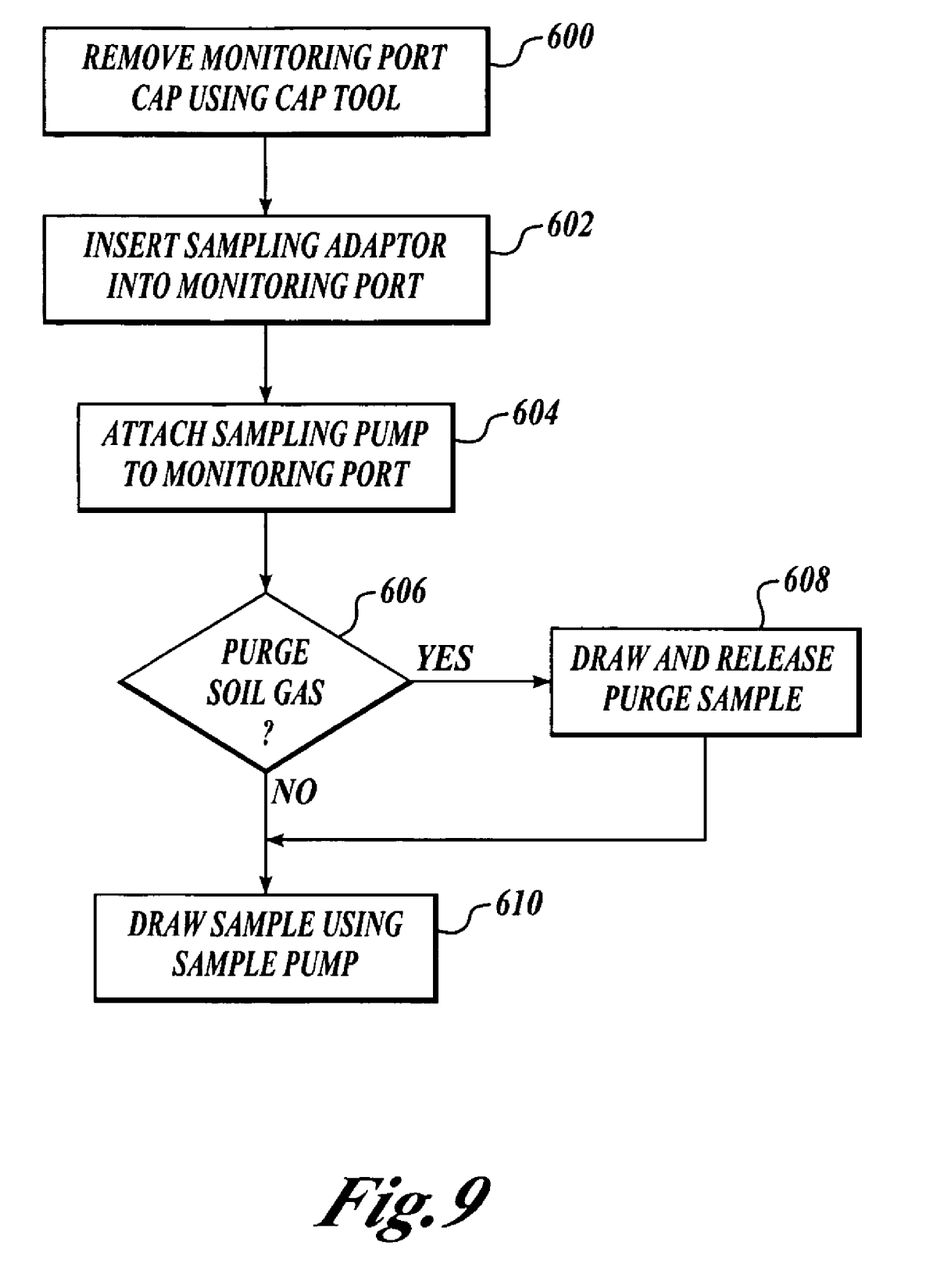
FIG. 9 is a flow chart showing the preferred VOC monitoring methodology of the present invention.

A preferred method for collecting soil vapor samples using the preferred soil probe 20 of the present invention is described with reference to FIGS. 1, 7 and 9. With reference to the flow chart shown in FIG. 9, at block 600, the monitoring cap 80 is removed from the monitoring port 30 using the cap tool 90. At block 602, the sampling adaptor 100 is inserted into the threaded locking aperture 38 of the monitoring port 30. This is accomplished by screwing the threaded first end 102 of the sampling adaptor along the threaded interior 42 of the locking aperture 38 of the mounting plate 32. The removal of the monitoring cap 80 and the insertion of the sampling adaptor 100 preferably occurs very quickly to minimize the potential exchange of undesirable materials or contaminants, such as gases, liquids or other particles, between the facility and the facility subsurface 170, particularly in the event that a one-way valve is not present in the interior of the threaded neck 44 to prevent undesirable materials from the facility passing through the monitoring port 30 into the subsurface 170 during operation of the system of the present invention. For the same reason, namely, to prevent the unintended exchange of undesirable materials between the facility and the facility subsurface 170, the sampling adaptor is preferably inserted with the shutoff valve 108 closed.

At block 604, a sampling pump 190 is attached to the second end 106 of the sampling adaptor 100. At decision block 606, a determination is made whether to purge the soil gas prior to withdrawing a sample for testing. It is frequently desirable to purge the soil probe 20 and subsurface 170 of possible atmospheric contaminants prior to withdrawing a sample for testing purposes. If the determination is made at decision block 606 to purge the soil gas, the logic proceeds to block 608. At block 608, the sampling pump 190 is initiated, the shutoff valve 108 is opened, a sample of the subsurface soil gas is withdrawn using the sampling pump, the shutoff valve 108 is closed, and the captured purge sample is released in a predetermined manner so as to avoid further possible soil gas contamination. The logic then proceeds to block 610. If the determination is made at decision block 606 not to purge the soil gas, for example if a purge process has already occurred, the logic proceeds directly to block 610. At block 610, the sampling pump 190 is initiated, the shutoff valve 108 is opened, a sample of the subsurface soil gas is withdrawn using the sampling pump and the shutoff valve 108 is closed. The resultant captured sample is subsequently tested.

As explained above, the top of the soil probe is designed to facilitate connection to a sampling device that withdraws vapors and gas from the soil beneath the facility surface. For example, a hand pump or other sampling device can be used to withdraw air from the soil probe. Soil gas VOC content is preferably measured in the field by using a hand pump connected to a variety of commercial calorimetric detector tubes or field instruments designed to measure VOC concentrations. Soil gas samples can also be collected in containers for later laboratory analysis and precise quantification of VOC concentration.

The subsurface 170 soil gas is preferably sampled on a routine basis, but sampling may also occur on an incidental basis as desired. Routine monitoring, annually or semiannually, is preferably established to determine if a release of VOC to the subsurface has occurred during the period. In addition, sampling events can take place in anticipation of property sale, renewal of insurance, or following a release incident to assess potential migration to the subsurface soil.

While the preferred embodiment of the invention has been illustrated and described, as noted above, many changes can be made without departing from the spirit and scope of the invention. For example, the precise components used in the preferred soil probe 20 may be modified in accordance with the overall function of the soil probe to safely withdraw soil gas samples. As discussed above, various types of sampling pumps may be used. The exact sequence of many of the steps in the installation and sampling methods may be altered and steps merged. For example, applying the VOC resistant sealant 180 in block 502 of FIG. 8 may occur concurrent with insertion of the monitoring port 20 in block 504. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A method for installing a volatile organic compound monitoring station for sampling soil gas in the subsurface under a facility, comprising:
    creating a surface penetration at a facility;
    positioning a securing member within the surface penetration;
    expanding the securing member to engage the securing member with a wall of the surface penetration;
    inserting a monitoring station into the surface penetration, the monitoring station comprising a mounting plate and a generally tubular member extending substantially perpendicularly from the mounting plate; and
    forming a seal between the monitoring station and the facility surface, wherein forming a seal between the monitoring station and the facility surface comprises applying a sealant to the facility surface substantially around the surface penetration to facilitate creation of the seal between the monitoring station and the facility surface and positioning the mounting plate on the seal having the generally tubular member extending into the penetration.

2. A soil probe for monitoring the subsurface under a facility surface for volatile organic compounds, comprising:
- a monitoring port having an end filter in communication with the subsurface under the facility surface, a mounting plate comprising an aperture, and a threaded neck secured to the mounting plate proximate the aperture;
- a monitoring port cap configured to close the monitoring port to minimize the movement of undesirable materials between the facility and the subsurface via the monitoring port;
- a sampling adaptor configured to interface with the monitoring port and a sampling pump to allow the withdrawal of a soil gas sample from the subsurface under the facility surface; and
- a securing member engaging the subsurface under the facility surface and having threads corresponding to and configured to interface with the threaded neck of the mounting plate to secure the mounting plate so that the end filter of the mounting plate extends into the subsurface under the facility surface.

3. A soil probe for monitoring the subsurface under a facility surface for volatile organic compounds, comprising:
- a monitoring port having an end filter in communication with the subsurface under the facility surface;
- a monitoring port cap configured to close the monitoring port to minimize the movement of undesirable materials between the facility and the subsurface via the monitoring port;
- a sampling adaptor configured to interface with the monitoring port and a sampling pump to allow the withdrawal of a soil gas sample from the subsurface under the facility surface; and
- wherein the monitoring port has a locking aperture; and
- further comprising a locking tool for use in the installation of the monitoring port, the locking tool having an end corresponding in size and shape to the locking aperture of the monitoring port.

4. A soil probe for monitoring the subsurface under a facility surface for volatile organic compounds, comprising:
- a monitoring port having an end filter in communication with the subsurface under the facility surface, a mounting plate comprising an aperture, and a neck secured to the mounting plate proximate the aperture;
- a monitoring port cap configured to close the monitoring port to minimize the movement of undesirable materials between the facility and the subsurface via the monitoring port, the monitoring port cap having a sealing element including a plurality of turning recesses formed therein;
- a cap tool for use in the installation of the monitoring port cap, the cap tool having a configuration engageable with the turning recesses of the sealing element, including a plurality of turning pins corresponding in size and shape to the turning recesses of the monitoring port cap; and
- a sampling adaptor configured to interface with the monitoring port and a sampling pump to allow the withdrawal of a soil gas sample from the subsurface under the facility surface.

* * * * *